United States Patent [19]

Bozich, Jr.

[11] Patent Number: 4,921,795
[45] Date of Patent: May 1, 1990

[54] METHOD FOR PRODUCING HIGH SOLIDS DEXTRIN ADHESIVES

[75] Inventor: Frank A. Bozich, Jr., Clarendon Hills, Ill.

[73] Assignee: North American Adhesive Company, Berkeley, Ill.

[21] Appl. No.: 28,655

[22] Filed: Mar. 20, 1987

[51] Int. Cl.$^5$ .................. C12P 19/20; C12P 19/14; C12N 9/28; C12N 9/32; C12N 9/34; C09J 3/06
[52] U.S. Cl. .................. 435/96; 435/99; 435/202; 435/204; 435/205; 106/210; 127/29; 127/38
[58] Field of Search .................. 435/98, 99, 201, 96, 435/202, 204, 205; 106/210

[56] References Cited

U.S. PATENT DOCUMENTS

| | | | |
|---|---|---|---|
| 2,609,326 | 9/1952 | Pigman et al. | 195/31 |
| 3,149,049 | 9/1964 | Walkup et al. | 195/31 |
| 3,414,467 | 12/1968 | Ferrara | 161/266 |
| 3,436,309 | 4/1969 | Ottinger | 195/31 |
| 3,450,549 | 6/1969 | Schwalbe | 106/210 |
| 3,728,140 | 4/1973 | Yoshida | 106/210 |
| 3,922,197 | 11/1975 | Leach et al. | 195/31 R |
| 4,014,743 | 3/1977 | Black | 195/31 R |
| 4,600,439 | 7/1986 | Schneider et al. | 106/139 |

OTHER PUBLICATIONS

Kirk-Othmer "Encyclopedia of Chemical Technology", vol. 21, 3rd Ed., pp. 492-496.

*Primary Examiner*—Thomas G. Wiseman
*Assistant Examiner*—Charles L. Patterson, Jr.
*Attorney, Agent, or Firm*—McAndrews, Held & Malloy, Ltd.

[57] ABSTRACT

The present invention relates to an improvement in the alpha-amylase method of hydrolyzing a heated slurry of raw starch into starch fragments, the improvement comprising adding a hydrolytically effective amount of the enzyme, glucoamylase, to the reaction slurry.

The present invention further relates to a method for the production of high solids dextrim adhesives from raw starch. In carrying out the invention, an aqueous slurry containing raw starch is subjected to hydrolysis at an elevated temperature by the action of two thermally stable enzymes, alpha-amylase and glucoamylase. Once the viscosity of the reaction slurry is reduced to 1000-2000 centipoise as determined by a Brookfield viscometer at 20 rpm, 100° F., and at 45-55% solids (approximately 2.5 hrs.), the enzymes are then inactivated and the reaction is complete. The rheological properties of the resulting slurry can be adjusted as needed.

The present invention is useful because it provides a more direct and economical method for hydrolyzing starch in general, and for producing dextrin adhesives directly from raw starch for use in the high speed paper coating industry in particular.

9 Claims, No Drawings

METHOD FOR PRODUCING HIGH SOLIDS DEXTRIN ADHESIVES

BACKGROUND OF THE INVENTION

A. Field of the Invention

The present invention relates to a method for hydrolyzing starch generally which eliminates the limit dextrin problem encountered in methods that employ the alpha-amylase enzyme. This invention further relates to an enzymatic process for the production of high solids dextrin adhesives directly from raw starch. The high solids dextrin adhesives produced by the disclosed method are useful in the high speed machine coating of paper, and also the wrinkle free conversion of paper to various end products such as envelopes and poster board.

Raw starch can be converted into a number of commercial products such as laundry starches, sizing for paper, and a variety of adhesives. Most of these commercial products require that the raw starch by hydrolyzed or cleaved into fragments. It is the size and shape of the fragments so produced which impart the properties that distinguish one starch product from another. This is especially true in the case of adhesives where particle size and shape will determine whether an adhesive is a low solids type suitable for the production of gypsum board or whether the adhesive is a high solids type suited for lay flat mounting or for the high speed machine application of envelope back gums.

Starch $(C_6H_{10}O_5)n$, is the principal reserve polysaccharide in plants. In plants, starch usually occurs as granules. Starch granules are broken down into useful commercial products, such as adhesives, based upon their physical or chemical properties or both.

One of the physical properties of the starch granule is its ability to gelatinize. Gelatinization is a process wherein hot water acts upon a slurry or aqueous suspension of starch granules to overcome hydrogen bonding within the granule causing the granules to swell. The temperature at which swelling begins to occur is the gelatinization temperature. As the temperature increases, there is an increase in the number and size of the swollen granules and a corresponding increase in the viscosity of the slurry. At first, the viscosity of the slurry increases rapidly. However, because the swollen granules are fragile and tend to fragment under the influence of shear in the cooking vessel, there is a corresponding reduction in viscosity with fragmentation. As a consequence of these competing effects, the viscosity of a heated slurry of starch granules increases rapidly when the gelatinization temperature is reached; peaks when fragmentation equals gelatinization; decreases as fragmentation becomes predominent over swelling, and finally stabilizes when both further swelling and fragmentation becomes negligible. The fragments that are produced by this process are called "solids". In any given reaction slurry, as the amount of fragmentation increases, the solids content of the slurry increases and its viscosity decreases. The production of reaction slurries having a high solids content is highly desirable in the paper adhesives industry.

The chemical properties of starch are based upon its structure. Amylose is the linear polymer of starch and it is composed exclusively of $\alpha$-D-glucopyranosyl units linked (1→4). Amylopectin, on the other hand, is the branched polymer of starch which is composed of $\alpha$-D-glucopyranosyl units linked (1→4) with (1→6) linkages creating the branch points.

B. Prior Art

The classic method for producing adhesives in general from an aqueous slurry of raw starch takes advantage of the physical properties of the starch granule. The classic method consists of heating the slurry of the raw starch to past its gelatinization point while subjecting the extremely long and highly viscous starch molecules to mechanical shearing action. The function of the shearing action is to break the long starch molecules into shorter and less viscous molecules without destroying the adhesiveness of the native starch molecule. Although this procedure is suited for the production of low solids adhesives, it is not suited to producing the high solids starch adhesives of the present invention. See: U.S. Pat. No. 3,450,549 (Schwalbe) at col. 2, ln. 1-4.

Pigman (U.S. Pat. No. 2,609,326) describes the early use of a single thermally stable enzyme, alpha-amylase, to depolymerize raw corn starch into a dry laundry starch product that is readily soluble in cold water. The enzyme, alpha amylase, acts upon a chemical property of the starch—the $\alpha(1\rightarrow4)$ linkage. Specifically, the enzyme, alpha amylase, partially depolymerizes the raw starch by randomly hydrolyzing only the $\alpha(1\rightarrow4)$ glucosidic linkages in the gelatinized starch granules.

Schwalbe (U.S. Pat. No. 3,450,549) describes the use of the thermally stable enzyme, alpha amylase, in the production of high solids dextrin adhesives. In Schwalbe, the alpha amylase enzyme is used to first subject the gelatinized native starch "to a regulated degree of hydrolysis", i.e.,—to a pre-determined reduction in viscosity. (Col. 2, ln. 22-24.) According to Schwalbe, complete enzymatic hydrolysis of the starch is undesirable because the hydrolysis process produces dextrinized products (limit dextrins) which materially reduce the bonding action of the starch adhesive. (Col. 2, ln. 53-59). Accordingly, the "regulated degree of enzymatic hydrolysis" described in Schwalbe consists of permitting the enzyme, alpha-amylase, to randomly cleave some linear starch fragments off both the outer branches of amylopectin starch molecules and off the linear amylose molecules. In Schwalbe, the critical step consists of preventing the alpha-amylase enzyme from cleaving all the linear fragments off the outer branches of the amylopectin molecule thereby producing a terminally branched limit dextrin—a large starch molecule whose terminal branches contain nonhydrolyzable $\alpha(1\rightarrow6)$ glucosidic linkages. (Col. 2, ln. 53-65).

In Schwalbe, upon achieving the "re gulated degree of enzymatic hydrolysis", the alpha-amylase enzyme is then denatured. Further breakdown of the starch molecules is then accomplished by employing a second step—a conventional mechanical shearing step (steam jetting or high speed agitation) which is conducted at temperatures in the range of 260°–300° F. until the desired reduction in viscosity is obtained. (Col. 3, ln. 11-19).

Black (U.S. Pat. No. 4,014,743) describes a continuous flow enzymatic process for decreasing the viscosity (thinning) of starch slurrys to eliminate problems resulting from the development of temporary peak viscosities during geletinization in the usual enzyme liquification procedures. Black's process consists of continuously adding the enzyme (alpha-amylase) and raw starch slurry to a gelatinized and partially converted reaction slurry so as to maintain a blend within the tank having a low enough viscosity to be agitated and pumped off. In a mechanical shearing step similar to that described in Schwalbe, Black mixes the effluent from the alpha-amylase conversion with steam in a jet mixer-heater at a temperature raised to 320° F. (Col. 7, ln. 44–47), further reducing viscosity. This step has the further function of denaturing the enzyme.

SUMMARY OF THE INVENTION

The present invention relates to an improvement in the alpha-amylase method of hydrolyzing raw starch into starch fragments in an aqueous reaction slurry heated to above 110° F., the improvement comprising adding a hydrolytically effective amount of the enzyme, glucoamylase, to the reaction slurry.

The present invention further relates to a method for the preparation of high solids dextrin adhesives from raw starch comprising the steps of preparing an aqueous reaction slurry comprising water, raw starch and a hydrolytically effective amount of the enzymes, alpha-amylase and glucoamylase, said water having a pH suitable for enzymatic hydrolysis;

heating said aqueous reaction slurry with stirring to a temperature suitable for enzymatic hydrolysis of said raw starch;

maintaining one of more ranges of temperatures suited for hydrolysis until the viscosity of said reaction slurry is reduced to a viscosity between about 1000–2000 centipoise as determined by a Brookfield viscometer at 20 rpm; 110° F., and at 45–55% solids when 0 to 10% sodium borate pentahydrate (based upon starch solids) is added to the slurry; and adjusting the pH of said aqueous reaction slurry sufficient to inactivate both said alpha-amylase and said glucoamylase enzymes, thereby preventing further reduction in the viscosity of said aqueous reaction slurry.

Unlike the mixed enzymatic and mechanical process of Schwalbe, the present invention effects the hydrolysis of the starch molecule by a completely enzymatic process. Whereas Schwalbe employes only a single enzyme, the present invention employs two enzymes, alpha-amylase and glucoamylase. In the present invention, the function of the second enzyme, glucoamylase, is to eliminate the limit dextrin problem described in Schwalbe and the mechanical shearing step.

As to the limit dextrin problem, the present invention permits the alpha-amylase enzyme to cleave the outer $\alpha(1 \to 4)$ linkages of the amylopectin molecule up to the $(1 \to 6)$ branch points so as to produce a limit dextrin. The second enzyme of the present invention, glucoamylase, then cleaves the terminal $\alpha(1 \to 6)$ glucosidic linkages of the limit dextrin, exposing linear chains of $\alpha(1 \to 4)$ linkages which may be further randomly cleaved into fragments by the alpha-amylase enzyme.

In further contrast, the present invention does not require the mechanical shearing step described and claimed in Schwalbe. Although the present invention employs stirring, the stirring employed is only that amount sufficient to create a vortex in the aqueous reaction slurry, thereby maintaining an adequate mix of enzyme with reactants. The mechanical shearing step described in Schwalbe consists of high speed mixing at several thousand rpms which is capable of ripping fragments off the large starch molecules. The mechanical shearing step is incompatible with the present invention since it would also have the additional effect of denaturing the enzyme molecules of the present invention which are themselves very large.

Moreover, the present invention does not employ the high temperatures 260°–300° F. required in Schwalbe. Although the present invention can function at the high temperatures described in Schwalbe, it is preferrable and more efficient to maintain temperatures in the aqueous reaction slurry just above the gelatinization temperature of the starch.

In Black, the resulting product is a blend of starches which are non-uniform with respect to chain length because of having been subjected to different degrees of enzyme conversion—hydrolysis before being pumped off (Col. 3, ln. 44). Although Black claims the ability to produce high solids liquification, the high solids of Black (20–40%) are substantially less than the high solids produced by the present invention. (35–80%). Moreover, because Black's process is continuous flow, Black's starch slurry is limited to 10–45% by weight starch on a dry solids basis. In contrast, the present invention typically employs an initial starch slurry that is 58% by weight starch on a dry solids basis.

Although Black addresses the problem of reducing sugars produced in the reaction slurry, Black at no time addresses the problem specifically solved by the present invention—the use of an enzyme, such as glucoamylase, to solve the limit dextrin problem that accompanies the alpha-amylase enzymatic hydrolysis of starch.

DETAILED DESCRIPTION OF THE INVENTION

The present invention relates to an improvement in the method of hydrolyzing a gelatinized slurry of starch granules employing the enzyme alpha-amylase, wherein the improvement comprises adding to the slurry hydrolytically effective amount of the enzyme glucoamylase. A problem encountered in hydrolyzing starch by means of the alpha-amylase enzyme alone is that alpha-amylase only cleaves $\alpha(1 \to 4)$ linkages—the linear glucosidic linkages of starch. The result of such alpha-amylase hydrolysis upon a slurry of gelantinized starch granules is that the linear amylose molecules of starch are randomly cleaved into starch fragments along their entire length, whereas in the larger and highly branched amylopectin molecules, only the outer linear portions of the molecule are cleaved with further cleavage being inhibited at the inersection of the first $\alpha(1 \to 6)$ branch points.

Typically in the alpha-amylase hydrolysis of starch, hydrolysis is permitted to occur just long enough to randomly cleave the linear amylose into suitably sized starch fragments while randomly cleaving the linear branches off the amylopectin molecule. The enzyme reaction is then stopped, and further breakdown of the remaining starch molecules into suitably sized fragments is accomplished by mechanical shearing.

If the alpha-amylese hydrolysis of the starch were permitted to continue, the result would be that the linear starch fragments would continue to be randomly cleaved into comparatively useless starch products, glucose and its dimer (maltose), whereas the highly branched amylopectin molecule upon being snipped to high molecular weight limit dextrin, would continue to resist further hydrolysis.

The present invention solves the limit dextrin problem produced during the alpha-amylase hydrolysis of starch. Specifically, the present invention solves the limit dextrin problem by employing a second thermally stable enzyme, glucoamylase. The glucoamylase enzyme is capable of cleaving the alpha-amylase inhibiting (1→6) branch points off of the exterior of the limit dextrins, thereby exposing lengths of linear α(1→4) linkages susceptible to further random cleavage by alpha-amylase until the next branch point is reached. Once a branch point is again exposed, the glucoamylase again cleaves the outer branch point, exposing further linear linkages susceptible to hydrolysis by the alpha-amylase enzyme. This process is permitted to continue until an optimal mix of fragment sizes is achieved. In the case of high solids dextrin adhesives, optimal fragment size is achieved when the viscosity of the aqueous starch reaction slurry is between about 1000-2000 centipoise as determined by a Brookfield viscometer at 20 rpm, 110° F., and at 45-55% solids typically about 0 to 10% sodium borate pentahydrate (based upon starch solids) is added to the slurry.

By employing the combination of enzymes disclosed in this invention, one can efficiently hydrolyze starch in a completely enzymatic process without the need to resort to high temperatures (220°-300° F.) and mechanical shearing techniques to further breakdown the starch. Moreover, this invention is particularly suited to native starches having a high amylopectin content, such as waxy maize, which are generally considered unsuitable for traditional starch hydrolysis techniques.

By employing the proper ratio of the enzymes alpha-amylase and glucoamylase, one can effectively eliminate the limit dextrin problem without producing excessive amounts of reducing sugars—an undesirable feature in adhesives.

By controlling the hydrolysis temperature and the amount of enzyme per pound of raw starch, it is possible to control the hydrolysis time. For example, in any given product situations, low hydrolysis temperatures and/or enzyme concentrations generally lead to longer hydrolysis times, whereas high hydrolysis temperatures and/or enzyme concentrations generally lead to shorter hydrolysis times. However, in both instances above, the same final product can be produced.

By increasing hydrolysis times at a particular temperature and at a particular enzyme amount, smaller sized starch fragments can be produced.

In a preferred embodiment of the present invention, said invention is particularly suited to the production of high solids dextrin adhesives from an aqueous reaction slurry containing raw starch. In said preferred embodiment, the concentration of the enzyme, alpha-amylase, per pound of raw starch is about 287-28,700 units/pound, more preferably 574-13,500 units/pound; whereas the concentration of the enzyme, glucoamylase, per pound of raw starch is preferably about 5.4-540 units/pound, more preferably 10.8-270 units/pound. Moreover, in said preferred embodiment, the ratio of the concentration of the enzyme, alpha-amylase, to the concentration of the enzyme, glucoamylase, is from about 33 to about 73, based upon enzyme activity as measured in units/ml. Further, in said preferred embodiment, the hydrolysis temperature is maintained preferably between about 120° F. to about 300° F., most preferaby between about 150° F. to about 220° F.

Because the reaction time is temperature dependent, it is preferred to measure the viscosity of the reaction slurry to determine completion. For high solids adhesives, the preferred final viscosity is between about 1000 to about 2000 centipoise as determined by a Brookfield viscometer at 20 rpm, 110° F., and at 45-55% solids, when 0-10% sodium borate pentahydrate (based upon starch solids) are added to the slurry.

The preferred pH ranges for the enzymes may vary depending upon the source of the enzymes. The enzymes are thermally stable and are available from commercial sources. For example, the thermally stable alpha-amylase enzyme, is derived from Bacillus stearothermophilus and is commercially available a ENZECO ® Thermolase from Enzyme Development of New York. Similarly, the thermally stable glucoamylase enzyme is derived from a strain of Aspergillus niger and is commercially available as ENZECO ® Glucoamylase from Enzyme Development of New York.

Among the raw starches suitable for hydrolysis into starch fragments by this method are the raw starches obtained from potato, rice, tapioca, corn, waxy maize, farina wheats, and the like.

DESCRIPTION OF THE PREFERRED EMBODIMENTS

The following example is given by way of illustration only and in no way should be construed as limiting the invention in spirit or in scope, as many modifications in materials and methods will be apparent from this disclosure to those skilled in the art.

EXAMPLE 1

Preparation of a High Solids Dextrin Adhesive from Raw Corn Starch

To 10 gal. of water maintained at 135° F. in a reaction vessel was added with mixing sufficient buffer to adjust the pH to 5.5-6.5. To the water was added 110 g of ENZECO ® Thermolase, an alpha-amylase enzyme having an activity of 2,872 units/g, and 27 g of ENZECO ® Glucoamylase, a glucoamylase enzyme having an activity of 220 units/g. (At this point, the ratio of said alpha-amylase enzyme to said glucoamylase enzyme is 53:1.) To this mixing enzyme solution was added 100 pounds (dry weight) of raw corn starch. (At this point, there is 2870 units of alpha-amylase and 54 units of glucoamylase per pound of raw starch.) The temperature of the reaction slurry was gradually increased from 135° F. to 165° F. over a 30 minute period. With continued mixing, the temperature was then raised to 180° F. and held there for approximately two hours. At this time the viscosity of the reaction slurry was between 1000-2000 centipoise as determined by a Brookfield Viscometer at 20 rpm, 110° F. and at 45-55% solids when 0-10% sodium borate pentahydrate (based upon starch solids) is added to the slurry. After the above time, the pH was adjusted to less than 4.0 and the temperature was held at 175° F. with stirring for 30 minutes, producing denaturization of the enzyme and permitting no further reduction in viscosity. To the reaction slurry was then added with mixing 11.8 pounds of sodium borate pentahydrate. The mixing was continued for 30 minutes or until the reaction slurry was smooth. The resulting reaction slurry, having a high solids content, was now suited for the addition of humectants, solids and preservatives and for aliquoting and dilution as needed, employing methods well known in the adhesives art.

When compared to a traditional method for producing high solids dextrin adhesives directly from an equal weight of commercially prepared dextrin, the slurry produced by the present invention required less salts and urea (humectants) to produce a comparable high solids dextrin adhesive having the same slow drying properties. (Table 1).

TABLE 1

| Ingredient | Weight of Ingredients (lbs.) | |
|---|---|---|
| | Raw Starch Enzyme Method | Dextrin Direct Method |
| Borax pentahydrate | 11.8 | 11.8 |
| MgCl$_2$ | 19.0 | 39.0 |
| Urea | 43.1 | 63.1 |

What is claimed is:

1. A method for the preparation of high solids dextrin adhesives from raw starch comprising the steps of:
   preparing an aqueous reaction slurry comprising water, raw starch, and a hydrolytically effective amount of the enzymes alpha-amylase and glucoamylase in combination at a ratio from about 33 to about 73 with respect to their relative activities, said water having a pH suitable for enzymatic hydrolysis;
   heating said aqueous reaction slurry with stirring to a temperature suitable for enzymatic hydrolysis of said raw starch;
   maintaining said hyrolysis temperature until the viscosity of said reaction slurry is reduced to a viscosity betwen about 1000-2000 centipoise as determined by a Brookfield viscometer at 20 rpm, 110° F., and at 45-55% solids; and
   adjusting the pH of said aqueous reaction slurry sufficient to inactivate both said alpha-amylase and said glucoamylase enzymes, thereby preventing further enzymatic reduction of the viscosity of said aqueous reaction slurry.

2. The method of claim 1 wherein said temperature suited for enzymatic hydrolysis ranges from about 120° F. to about 300° F.

3. The method of claim 1 wherein said hydrolytically effective amount of said alpha-amylase enzyme in said aqueous reaction slurry is from about 287 to about 28,700 units per pound of raw starch (dry weight).

4. The method of claim 1 wherein said hydrolytically effective amount of said glucoamylase enzyme in said aqueous reaction slurry is from about 5.4 to about 540 units per pound of raw starch (dry weight).

5. The method of claim 1 wherein said temperature suited for enzymatic hydrolysis range from about 150° F. to about 220° F.

6. The method of claim 1 wherein said hydrolytically effective amount of said alpha-amylase enzyme in said aqueous reaction slurry is from about 574 to about 13,500 units per pound of raw starch (dry weight).

7. The method of claim 1 wherein said hydrolytically effective amount of said glucoamylase enzyme in said aqueous reaction slurry is from about 10.8 to about 270 units per pound of raw starch (dry weight).

8. The method of claim 1 wherein the hydrolytically effective amounts of said alpha-amylase enzyme to said glucoamylase enzyme, based upon enzyme activities, is a ratio ranging from about 43 to about 63.

9. The method of claim 1 wherein the source of said starch is a member of the group consisting of potato, rice, tapioca, corn, waxy maize, and farina wheats.

* * * * *